United States Patent
Ujhelyi et al.

(10) Patent No.: US 6,728,574 B2
(45) Date of Patent: Apr. 27, 2004

(54) SYSTEM AND METHOD FOR PATIENT-CONTROLLED RELIEF OF PAIN ASSOCIATED WITH ELECTRICAL THERAPIES

(75) Inventors: Michael R. Ujhelyi, Maple Grove, MN (US); Rahul Mehra, Stillwater, MN (US)

(73) Assignee: Medtronic, Inc., Minneapolis, MN (US)

( * ) Notice: Subject to any disclaimer, the term of this patent is extended or adjusted under 35 U.S.C. 154(b) by 258 days.

(21) Appl. No.: 10/040,147

(22) Filed: Oct. 19, 2001

(65) Prior Publication Data

US 2003/0078632 A1 Apr. 24, 2003

(51) Int. Cl.[7] ................................................. A61N 1/00
(52) U.S. Cl. ............................................................ 607/3
(58) Field of Search ....................................... 607/2–76

(56) References Cited

U.S. PATENT DOCUMENTS

| | | | |
|---|---|---|---|
| 3,311,111 A | 3/1967 | Bowers | 128/422 |
| 3,805,796 A | 4/1974 | Terry, Jr. et al. | 128/419 P |
| 4,223,679 A | 9/1980 | Schulman et al. | 128/419 PT |
| 4,987,897 A | 1/1991 | Funke | 128/419 PG |
| 5,119,832 A | 6/1992 | Xavier | 128/786 |
| 5,269,301 A | 12/1993 | Cohen | 607/6 |
| 5,405,362 A | 4/1995 | Kramer et al. | 607/5 |
| 5,674,249 A | * 10/1997 | de Coriolis et al. | |
| 5,683,432 A | 11/1997 | Goedeke et al. | 607/32 |
| 5,817,131 A | 10/1998 | Elsberry et al. | 607/5 |
| 5,843,139 A | 12/1998 | Goedeke et al. | 607/32 |
| 5,893,881 A | 4/1999 | Elsberry et al. | |
| 5,925,066 A | 7/1999 | Kroll et al. | |
| 5,987,356 A | * 11/1999 | DeGroot | |
| 6,086,582 A | 7/2000 | Altman et al. | 606/41 |
| 6,453,195 B1 | * 9/2002 | Thompson | |

FOREIGN PATENT DOCUMENTS

| | | | |
|---|---|---|---|
| EP | 0 870 518 A1 | 10/1998 | A61N/1/39 |
| WO | WO 01/28609 | 4/2001 | A61M/5/00 |
| WO | WO 02/074386 | 9/2002 | A61N/1/30 |

* cited by examiner

Primary Examiner—Scott M. Getzow
(74) Attorney, Agent, or Firm—Girma Wolde-Michael; Paul H. McDowall

(57) ABSTRACT

A pain management system that enables a patient to control pain associated with the application of electrical therapies by an implanted device that includes using a non-implanted drug delivery device. In an example embodiment, a pain management system includes an implanted medical device that detects an arrhythmia of a heart and telemetrically communicates from the implanted medical device an arrhythmia condition. The system also includes an external drug delivery arrangement that receives telemetric communications on the arrhythmia condition from the implanted device and provides an alert of the arrhythmia condition to the patient. The external drug delivery arrangement communicates to the implanted device that a drug is being administered to the patient. The implanted medical device includes a capacitive circuit that delivers the electrical therapy to the heart in response to the drug being administered.

12 Claims, 2 Drawing Sheets

SYSTEM AND METHOD FOR PATIENT-CONTROLLED RELIEF OF PAIN ASSOCIATED WITH ELECTRICAL THERAPIES

FIELD OF THE INVENTION

The present invention generally relates to the management of pain associated with applying electrical cardioversion therapies. In particular, the invention relates to patient-controlled pain suppression via patient administered sedation.

BACKGROUND OF THE INVENTION

Implanted medical devices are capable of detecting and treating an arrhythmia (i.e., irregular heartbeats) in a patient. In one example, the implanted medical device includes a defibrillator that applies an electrical pulse therapy to a patient's heart upon detecting fibrillation (i.e., high, irregular heartbeat), a form of arrhythmia. Cardioverters or defibrillators discharge relatively high energy electrical shocks or pulses into or across cardiac tissue to arrest a life-threatening atrial or ventricular fibrillation upon detection by the implanted medical device. Defibrillation shocks, while highly effective at arresting the fibrillation, may occur suddenly and can cause considerable patient discomfort.

Currently, defibrillation shock induced discomfort is managed with concomitant intravenous sedation. Intravenous sedation therapies require close medical supervision because the sedative agents cause a loss of consciousness and a lower respiration rate. Hence, sedative agents are not used by ambulatory patients to provide relief from defibrillation induced discomfort without medical supervision.

Ambulatory patients can administer oral sedatives (e.g., narcotics) at home to reduce patient discomfort. However, oral sedatives can incapacitate the patient for long periods of time and reaction time to the sedative is uncertain because the absorption rate varies between patients. With an oral sedative it is also difficult for the patient to synchronize the time of the shock delivery with the maximum sedative effect. In some cases, the patient may fall asleep even before activating the defibrillator. Traditional oral medications can also be misused/abused irrespective of detecting the arrhythmia. Intranasal narcotics are available but they only slightly reduce patient discomfort associated with the defibrillation shock.

Accordingly, there is a need for a system for enabling a patient to effectively control the pain associated with an electrical therapy via patient administered sedation. An approach that addresses the aforementioned problems, as well as other related problems, is therefore desirable.

SUMMARY OF THE INVENTION

Various embodiments of the present invention are directed to addressing various needs in connection with patient-controlled pain suppression of an electrical therapy using a non-implanted drug delivery device.

One embodiment of the invention is directed to a system for patient management of pain associated with an electrical therapy. The pain management system includes an implanted medical device that detects an arrhythmia of a heart and telemetrically communicates from the implanted medical device an arrhythmia condition. The system also includes an external drug delivery arrangement that receives telemetric communications on the arrhythmia condition from the implanted device and provides an alert of the arrhythmia condition to the patient. The external drug delivery arrangement communicates to the implanted device information that a drug has been administered to the patient. The implanted medical device includes a capacitive circuit that delivers the electrical therapy to the heart in response to the drug being administered.

In a related embodiment, the implanted device includes a stimulator circuit that delivers an electrical therapy to a selected portion of the patient's body. Upon detecting an irregularity (an irregularly operating body function) at the selected portion, an external drug delivery arrangement receives telemetric communications from the implanted device of the irregularity and provides an alert of the irregularity to the patient. The external drug delivery arrangement communicates to the implanted device that a drug is being administered to the patient. The stimulator circuit delivers the electrical therapy to the selected body portion in response to the drug being reacted to by the patient.

Another embodiment of the invention is directed to a system and a method for patient management of pain associated with an electrical defibrillation therapy. The pain management system includes an implanted cardiac defibrillator (ICD) device having a circuit that detects fibrillation of a heart and a circuit that telemetrically communicates from the ICD device a fibrillation condition of the heart. The system includes an external drug delivery arrangement that receives telemetric communications on the fibrillation condition of the heart and provides an alert of the fibrillation condition to the patient. The external drug delivery arrangement communicates to the ICD that the drug is being administered and that the drug is being reacted to by the patient. The system also includes a drug interaction verification circuit that provides an alert to the external drug delivery arrangement in response to the reaction to the drug. The implanted device includes a capacitive circuit that delivers the electrical therapy in response to the reaction to the drug.

The above summary of the present invention is not intended to describe each illustrated embodiment or every implementation of the present invention. The figures in the detailed description that follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
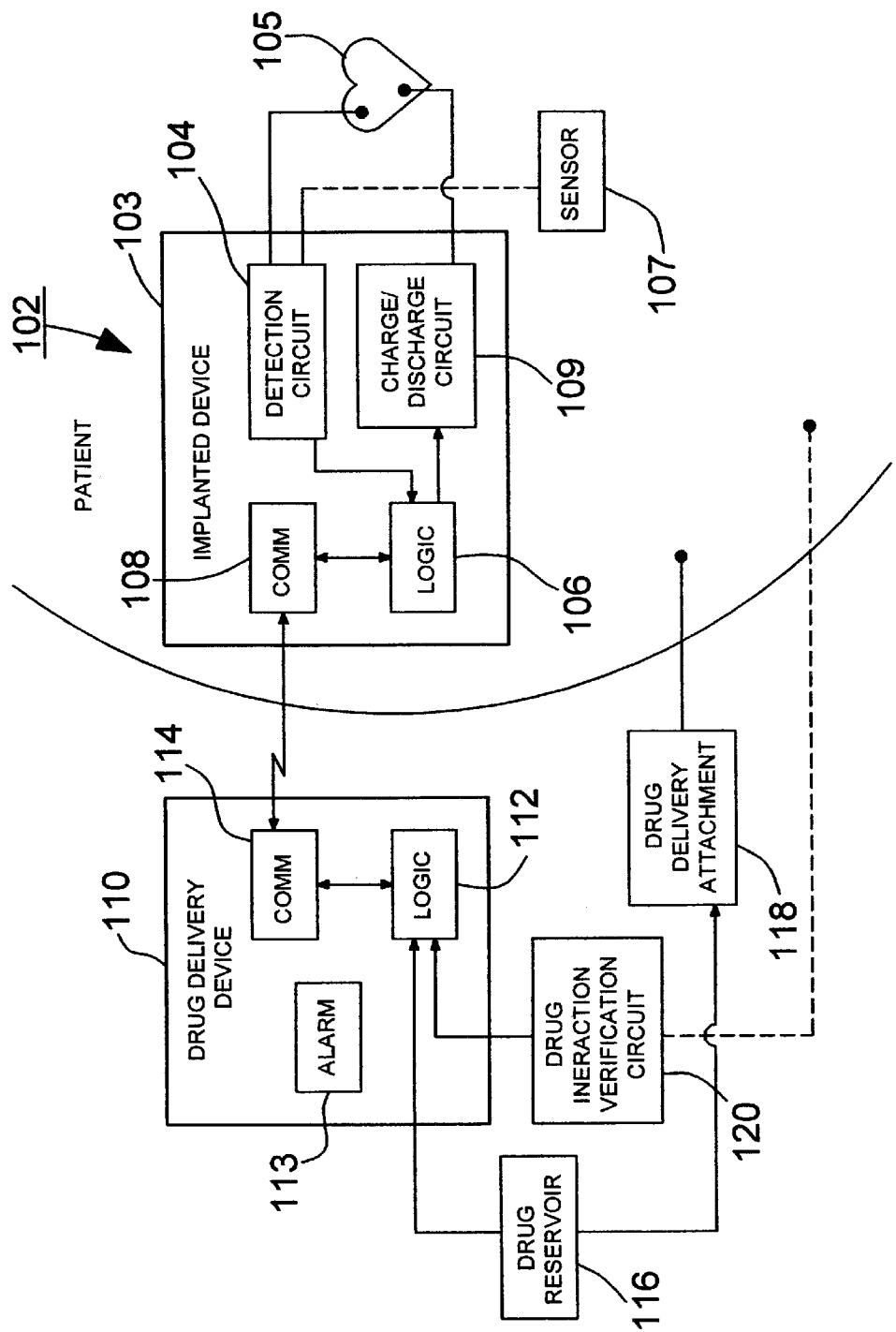
FIG. 1 illustrates a block diagram of a patient-controlled pain management system according to an example embodiment of the invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

The present invention is generally directed to a system that enables a patient with an implanted medical device to manage pain associated with an electrical therapy by using a non-implanted drug delivery device that communicates with the implanted medical device. In one example, the non-implanted drug delivery device and the implanted device establish two-way communications to coordinate applying the electrical therapy with the administration of a drug to the patient. While the present invention is not necessarily limited to such an application, the invention will be better appreciated using a discussion of example embodiments in such a specific context.

In an example embodiment of a patient-controlled pain management system, an implanted cardiac defibrillator (ICD) device detects fibrillation of a patient's heart and a capacitive circuit delivers an electrical therapy to the heart. The implanted device also telemetrically communicates a fibrillation condition of the heart to an inhalation device that the patient is carrying. The inhalation device receives the telemetric communications from the implanted device of the fibrillation condition and provides an alert (e.g., beeping sound or vibration) of the fibrillation condition to the patient. The patient then inhales a drug from a reservoir of the inhalation device, after which the inhalation device automatically communicates to the ICD that the drug has been administered. In this example, inhaling the drug triggers a timing circuit in the inhalation device that gives the patient time to absorb the drug before applying any electrical therapy. The implanted device delivers an electrical shock to the patient's heart in response to a message from the inhalation device that the time on the timing circuit expired.

In a related embodiment, the inhalation device and the implanted device coordinate applying the electrical therapy with a mechanical pressure switch that is gripped and depressed by the patient upon inhaling the drug. As the drug is reacted to, the patient loosens the grip on the pressure switch and triggers a signal to the inhalation device that the patient is ready for the electrical shock. The implanted device delivers the electrical shock after receiving telemetrically a message from the inhalation device that the drug has reacted with the patient. In another related embodiment, an external drug delivery device includes a relaxation monitoring arrangement for detecting when a patient is in a relaxed mode or in a sleep mode. The implanted device delivers the electrical therapy after the patient is asleep.

In another related embodiment, the implanted medical device includes a programmable locking feature that prevents the patient from using the external drug delivery device until an arrhythmia is first detected by the implanted device.

FIG. 1 illustrates a block diagram of a patient-controlled, pain management system 100 according to an example embodiment of the invention. A patient 102 has an implanted medical device 103 that detects abnormal body function, such as an arrhythmia (irregular heartbeat) of a heart 105. In this example, a detection circuit 104 detects an atrial fibrillation of the heart and transmits a warning signal via a communications module 108 to an inhalation drug delivery device 110. Inhalation device 110 sounds an audible alarm or signal (or vibrates) in response to the warning signal from implanted device 103 alerting patient 102 that his heart is in atrial fibrillation. Patient 102 inhales a sedative drug from a drug canister or reservoir 116 via a drug delivery attachment 118 (e.g., mask or mouthpiece). Upon inhaling the sedative, inhalation device 110 automatically communicates to implanted device 103 that patient 102 has taken the sedative. In this example embodiment, inhaling the sedative also triggers a timing circuit in inhalation device 110 that operates an internal clock for a selected time period. Once the clock expires, inhalation device 110 transmits another signal to implanted device 103 that time has expired. In response, implanted device 103 applies an electrical therapy to heart 105 via a charging/discharging circuit 109.

Heart conditions detectable by detection circuit 109 include, but are not limited to, ventricular fibrillation, tachycardia, bradycardia and eventual heart failure. In a related embodiment, a logic unit 106 in conjunction with detection circuit 104, evaluate the severity of the detected heart condition. Logic unit 106 continues to monitor the general condition of heart 105 before triggering detection circuit 104 to warn patient 102 of a detected arrhythmia.

In a related embodiment, the timing circuit is disposed within the implanted device and a signal from inhalation device 110 triggers the timing circuit. Because drug interaction can vary from one patient to another, the physician that programs the implanted device also programs the timing circuit in either the inhalation device or the implanted device. In setting the time period, the physician may factor in the type of sedative used and an absorption rate that varies as a function of the size, weight, age and gender of the patient.

In the present embodiment, inhalation drug delivery device 110 is comprised of a communications module 114 that communicates bi-directionally with implanted device 103 via communications module 108. The drug canister contains the volatile/gaseous agent (e.g. nitrous oxide) and upon discharge is disposable and replaceable with a fully charged canister. Drug delivery device 110 also includes a logic unit 112 (e.g. microprocessor) that meters the dose and controls communications with implanted device 103. Unit 112 also processes warning signals from implanted device 103 and transmits them to an alarm unit 113 that audibly advises patient 102 of the bidirectional communication occurring between implanted device 103 and drug delivery device 110. When drug reservoir 116 and drug delivery attachment 118 deliver the sedative to the patient in a prescribed dosage, logic unit 112 transmits this information via module 114 to implanted device 103. In this embodiment, the drug delivery to the patient triggers either the timing circuit in delivery device 110 or a timing circuit in implanted device 103. Once time has expired, implanted device 103 delivers the electrical therapy. Implanted device 103 is programmed to automatically deliver additional electrical therapies or shocks if the preceding shock was either ineffective or an atrial tachyarrhythmia recurred prematurely.

In a related embodiment, the patient is audibly warned (or via a vibration or light signal) by drug delivery device 110 that the electrical therapy is to be administered shortly. In another related embodiment, drug delivery device 110 has a locking feature to prevent administering doses too close in succession.

In another embodiment, pain management system 100 includes a drug interaction verification circuit 120 that provides feedback to system 100 as to the patient's reaction to the sedation therapy before applying the electrical therapy. Drug interaction verification circuit 120 (hereinafter "verification circuit") interfaces with patient 102 to alert external drug delivery device 110 when the patient reacts to the sedative. Upon receiving an alert from verification circuit 120, external drug delivery device 110 alerts implanted device 103 that the sedative is taking effect in the patient and the electrical therapy can proceed. In a related embodiment, verification circuit 120 is communicatively coupled to implanted device 103 such that the implanted device receives immediate feedback that the sedative is taking effect in the patient.

In one example embodiment, verification circuit 120 includes a mechanical pressure switch or lever that the patient actuates upon drug administration. At first the patient grips the lever and continues to hold until the sedative takes effect. The patient eventually looses the grip on the lever and the lever opens, thereby indicating that the sedative is taking effect. The opening of the lever relays a signal to implanted device 103, either directly or via external drug delivery device 110. Implanted device 103 delivers the electrical therapy in response to the release of the pressure switch.

In a related embodiment, verification circuit 120 includes a physiologic measuring arrangement that measures a concentration of a sedative in the bloodstream of the patient and detects when the drug concentration meets or exceeds a selected threshold or MAC (minimal alveoli concentration). Upon meeting/exceeding the selected threshold or MAC, implanted device 103 delivers the electrical therapy. In one application, patient 102 inhales nitrous oxide from reservoir 116 via a mask or mouthpiece (i.e., attachment 118). Verification circuit 120 measures the amount of nitrous oxide ($N_2O$) via the mask as the patient is exhaling. Once the patient's exhaled nitrous oxide level is at or about 70% (selected threshold level), verification circuit 120 communicates to implanted device 103 that sedation is taking effect and patient is ready to receive delivery of the electrical therapy.

In another related embodiment, the physiologic measure is combined with a timing circuit to ensure MAC is at a steady state level for a certain period of time before delivering the electrical therapy. This approach prohibits delivering the electrical therapy when the patient has just reached MAC and the mask is accidentally removed. In this situation, the patient may prematurely receive the electrical therapy without being adequately sedated.

In a related embodiment, implanted device 103 comprises a neurological implant or nerve stimulator that includes a stimulator circuit. Implanted device logic unit 106 coordinates with detection circuit 104 and at least one sensor 107 to detect irregular body functions at or near the area of the implant. Upon detecting an irregularity at the implant area, external drug delivery device 110 receives telemetric communications from implanted device 103 of the irregularity and provides an alert to the patient. Upon the patient receiving the drug, external drug delivery device 110 communicates this information to implanted device 103. The stimulator circuit then delivers the electrical therapy to the area to be stimulated.

In various embodiments described above, the sedation is deliverable orally, nasally (spray, mask or misting bottle), occularly or transcutaneously.

In the various embodiments described herein, modules 108 and 114 are configured to telemetrically communicate with each other using various techniques, including magnetic-field coupling, reflected impedance coupling and radio-frequency (RF) coupling. For more information regarding magnetic-field coupling, reference may be made to U.S. Pat. No. 3,311,111 to Bower and U.S. Pat. No. 3,805,796 to Terry et al., which are assigned to the assignee of the present invention and incorporated herein by reference. For more information regarding reflected-impedance coupling, reference may be made to U.S. Pat. No. 4,223,679 to Schulman et al., which is assigned to the assignee of the present invention and incorporated herein by reference. For more information regarding RF coupling, reference may be made to U.S. Pat. No. 5,843,139 to Goedeke et al., which is assigned to the assignee of the present invention and incorporated herein by reference.

Figure 2:
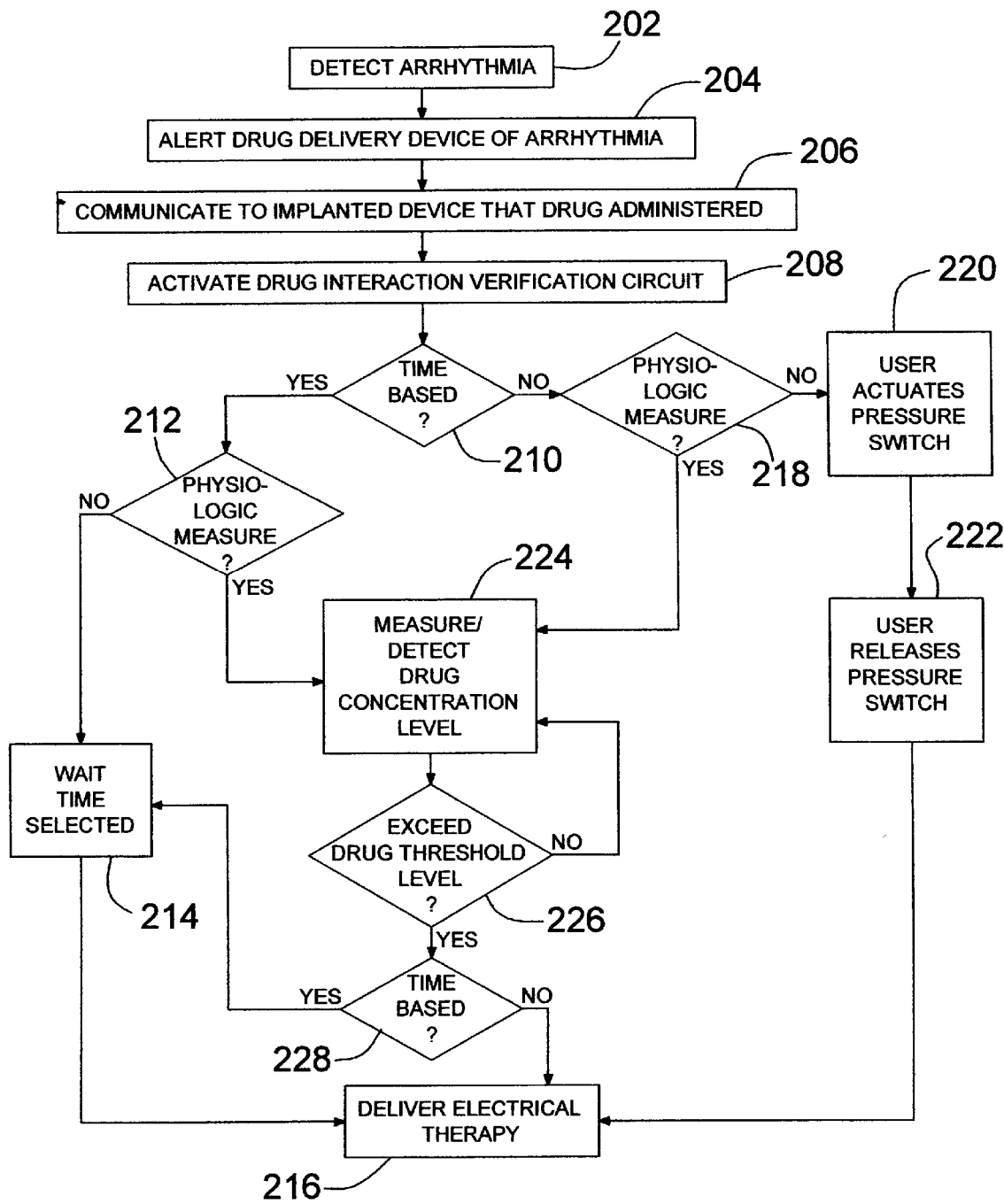
FIG. 2 is a flow diagram illustrating the manner of using a non-implanted drug delivery device to control pain associated with an electrical therapy according to another example embodiment of the invention.

Referring now to FIG. 2, a flow diagram 200 illustrates another manner of using a non-implanted drug delivery device 110 to control pain associated with an electrical therapy according to an example embodiment of the invention. At step 202, implanted device 103 detects an arryhthmia and then alerts drug delivery device 110 of the arrhythmia at step 204. Drug delivery device 110 then audibly (or, for example, emitting a vibration) warns the patient of the arrhythmia. The patient inhales the sedative through drug delivery device 110 and device 110 automatically communicates to implanted device 103 at step 206 that the patient has administered the drug. At step 208, the patient activates drug interaction verification circuit 120. If at step 210 verification circuit 120 is time based then at step 212 verification circuit 120 determines whether to physiologically measure the drug interaction. If at step 214 the drug interaction is not physiologically measured then circuit 120 times out and implanted device 103 delivers the electrical therapy at step 216.

If at step 210, verification circuit is not time-based then at step 218 verification circuit 120 determines whether to physiologically measure the drug interaction. If at step 220 the drug interaction is not physiologically measured then circuit 120 determines that the patient is actuating a pressure switch or lever to indicate when the sedation takes effect. At step 222 the patient releases the pressure switch, which indicates that the patient is reacting to the sedation. At step 216, implanted device 103 delivers the electrical therapy after receiving a feedback signal from verification circuit 120.

If at step 212, verification circuit 120 determines to also physiologically measure the drug interaction (e.g., nitrous oxide), then at step 224 verification circuit 120 detects and measures the concentration of sedative in the patient. In this example, the physiological measure will have a time component, as described in connection with FIG. 1, to ensure that the patient is at MAC before delivering the electrical therapy.

Similarly, if at step 218 verification circuit 120 determines to physiologically measure the drug interaction, then at step 224 verification circuit 120 detects and measures the concentration of sedative in the patient. In the example application where nitrous oxide is the chosen sedative, at step 226 verification circuit 120 determines whether the patient meets/exceeds the MAC level (threshold level). If at step 226, verification circuit 120 determines that the MAC level is met or exceeded then verification circuit 120 determines if a time component exists at step 228. If there is no time component at step 228, the implanted device delivers the electrical therapy at step 216. If at step 226, verification circuit 120 determines that the MAC level is not met or exceeded then the verification circuit continues to monitor the drug concentration level.

If there is a time component at step 228, then verification circuit 120 waits the selected time before communicating to the implanted device to deliver the electrical therapy. Implanted device 103 then delivers the electrical therapy at step 216.

In one example embodiment, external drug delivery device 110 includes a display (LCD or LED), used in conjunction with the audible/vibration/visual signaling, for alphanumeric messaging between the implanted device and the drug delivery device.

The present invention is compatible with a number of other implanted medical devices, such as drug pumps, neurological implants, nerve stimulators, various cardiac implants and equivalent medical devices.

Various modifications, equivalent processes, as well as numerous structures to which the present invention may be applicable will be readily apparent to those of skill in the art to which the present invention is directed upon review of the present specification. The claims are intended to cover such modifications and devices.

We claim:

1. A system for patient management of pain associated with an electrical therapy, the system comprising:
   an implanted medical device adapted to detect arrhythmia of a heart and to telemetrically communicate from the implanted medical device an arrhythmia condition; and
   an external drug-delivery arrangement adapted to:
      receive telemetric communications on the arrhythmia condition in response to the implanted medical device,
      provide an alert of the arrhythmia condition, and
      communicate to the implanted device that a drug has been administered,
   wherein the implanted medical device includes a capacitive circuit adapted to deliver an electrical therapy to the heart in response to the drug being administered and further comprising a drug interaction verification circuit adapted to physiologically measure a drug concentration in a user and detect when the drug concentration has exceeded a selected threshold in response to the external drug-delivery arrangement.

2. A system for patient management of pain associated with an electrical therapy, the system comprising:
   an implanted medical device adapted to detect arrhythmia of a heart and to telemetrically communicate from the implanted medical device an arrhythmia condition; and
   an external drug-delivery arrangement adapted to:
      receive telemetric communications on the arrhythmia condition in response to the implanted medical device,
      provide an alert of the arrhythmia condition, and
      communicate to the implanted device that a drug has been administered,
   wherein the implanted medical device includes a capacitive circuit adapted to deliver an electrical therapy to the heart in response to the drug being administered;
      wherein the implanted device is selected from the group consisting of an implanted cardiac defibrillator and a pacing device and
      further comprising a drug interaction verification circuit adapted to interact with a user of the implanted device and alert the external drug delivery arrangement in response to the user having reacted to the drug.

3. The system of claim 2, wherein the drug interaction verification circuit further comprises a mechanically actuated pressure switch adapted to be operated by the user in response to the drug administration, wherein the delivery of the electrical therapy is delivered in response to the release of the pressure switch.

4. The system of claim 2, wherein the drug interaction verification circuit further comprises a physiologic measuring arrangement adapted to measure a drug concentration in the user and detect when the drug concentration has exceeded a selected threshold, wherein the delivery of the electrical therapy is delivered in response to exceeding the selected threshold of drug concentration.

5. The system of claim 2, wherein the drug interaction verification circuit further comprises a physiologic monitoring arrangement that includes a relaxation monitor adapted to detect when a patient is in a relaxed mode.

6. A system for patient management of pain associated with an electrical therapy, the system comprising:
   an implanted medical device adapted to detect arrhythmia of a heart and to telemetrically communicate from the implanted medical device an arrhythmia condition; and
   an external drug-delivery arrangement adapted to:
      receive telemetric communications on the arrhythmia condition in response to the implanted medical device,
      provide an alert of arrhythmia condition, and
      communicate to the implanted device that a drug has been administered,
   the implanted medical device including a capacitive circuit adapted to deliver an electrical therapy to the heart in response to the drug being administered and wherein the external drug delivery arrangement is configured to physiologically deliver drugs via at least one mode selected from the group consisting of: oral, inhalation, nasal and occular.

7. A system for patient management of pain associated with an electrical therapy, the system comprising:
   an implanted medical device adapted to detect arrhythmia of a heart and to telemetrically communicate from the implanted medical device an arrhythmia condition; and
   an external drug-delivery arrangement adapted to:
      receive telemetric communications on the arrhythmia condition in response to the implanted medical device,
      provide an alert of the arrhythmia condition, and
      communicate to the implanted device that a drug has been administered,
   the implanted medical device including a capacitive circuit adapted to deliver an electrical therapy to the heart in response to the drug being administered and wherein the implanted device is adapted to prevent activation of the external drug delivery arrangement until an arrhythmia has been detected via a programmable locking arrangement.

8. A system for patient management of pain associated with an electrical defibrillation therapy, the system comprising:
   an implanted cardiac defibrillator (ICD) device adapted to detect fibrillation of a heart and to telemetrically communicate from the ICD device a fibrillation condition;
   an external drug delivery arrangement adapted to:
      receive telemetric communications on the fibrillation condition in response to the implanted medical device,
      provide an alert of the fibrillation condition, and
      communicate to the ICD that a drug has been administered and
      that the drug has been reacted to; and
   a drug interaction verification circuit adapted to provide an alert to the external drug delivery arrangement in response to reaction to the drug, the implanted medical device including a capacitive circuit adapted to deliver an electrical therapy to the heart in response to the drug interaction verification circuit.

9. The system of claim 8, wherein the drug interaction verification circuit includes a timing circuit adapted to trigger the electrical therapy at the end of a selected period in response to the drug administration.

10. The system of claim 8, wherein the drug verification circuit further comprises a mechanically actuated pressure switch adapted to be operated by a user in response to the drug administration, wherein the delivery of the electrical therapy is delivered in response to the release of the pressure switch.

11. The system of claim 8, wherein the drug interaction verification circuit further comprises a physiologic measuring arrangement adapted to measure a drug concentration in the user and detect when the drug concentration has exceeded a selected threshold, wherein the delivery of the electrical therapy is delivered in response to exceeding the selected threshold of drug concentration.

12. The system of claim 8, wherein the alert provided by the external drug delivery arrangement is selected from the group consisting of: audible, vibration, visual display and light.

* * * * *